US008556191B2

(12) United States Patent
Duru et al.

(10) Patent No.: US 8,556,191 B2
(45) **Date of Patent: *Oct. 15, 2013**

(54) SPRAY HEAD INCLUDING A SONOTRODE

(75) Inventors: Nicolas Duru, Paris (FR); Marion Prunier, Croissy sur Seine (FR); Pascal Tierce, Bondues (FR)

(73) Assignee: L'OREAL, Paris (FR)

( * ) Notice: Subject to any disclaimer, the term of this patent is extended or adjusted under 35 U.S.C. 154(b) by 122 days.

This patent is subject to a terminal disclaimer.

(21) Appl. No.: 12/370,136

(22) Filed: Feb. 12, 2009

(65) Prior Publication Data

US 2009/0200395 A1 Aug. 13, 2009

Related U.S. Application Data

(60) Provisional application No. 61/033,332, filed on Mar. 3, 2008.

(30) Foreign Application Priority Data

Feb. 13, 2008 (FR) ...................................... 08 50927

(51) Int. Cl.
*B05B 17/06* (2006.01)
*B05B 1/08* (2006.01)
*A61M 11/06* (2006.01)
*A61M 11/00* (2006.01)

(52) U.S. Cl.
USPC ..................... 239/102.2; 239/102.1; 239/370; 128/200.16

(58) Field of Classification Search
USPC ....................... 239/102.2, 102.1, 699, 370, 4; 128/200.14, 200.16, 200.18
See application file for complete search history.

(56) References Cited

U.S. PATENT DOCUMENTS

| | | | | | |
|---|---|---|---|---|---|
| 2,766,064 | A | | 10/1956 | Schweitzer | |
| 3,904,896 | A | | 9/1975 | Guntersdorfer | |
| 3,970,250 | A | | 7/1976 | Drews | |
| 4,153,201 | A | * | 5/1979 | Berger et al. | 239/102.2 |
| 4,301,968 | A | * | 11/1981 | Berger et al. | 239/102.2 |
| 4,523,080 | A | | 6/1985 | Bolton | |
| 4,540,123 | A | | 9/1985 | Junger et al. | |
| 4,541,564 | A | * | 9/1985 | Berger et al. | 239/102.2 |
| 4,702,418 | A | | 10/1987 | Carter et al. | |
| 4,723,708 | A | | 2/1988 | Berger et al. | |
| 4,796,807 | A | * | 1/1989 | Bendig et al. | 239/102.2 |
| 4,850,534 | A | * | 7/1989 | Takahashi et al. | 239/102.2 |

(Continued)

FOREIGN PATENT DOCUMENTS

| | | |
|---|---|---|
| DE | 2 165 609 A1 | 7/1973 |
| DE | 2 165 725 A1 | 7/1973 |

(Continued)

OTHER PUBLICATIONS

French Search Report from French Application No. FR 08 50930 filed Feb. 13, 2008.

(Continued)

*Primary Examiner* — Darren W Gorman
(74) *Attorney, Agent, or Firm* — O'Brien Jones, PLLC

(57) ABSTRACT

A device for spraying a cosmetic composition may include a sonotrode, the sonotrode having an end collar defining an ejection surface for ejecting particles of composition, the collar being suitable for bending under the effect of vibration of the sonotrode.

18 Claims, 6 Drawing Sheets

(56) References Cited

U.S. PATENT DOCUMENTS

| | | | | |
|---|---|---|---|---|
| 4,976,259 | A * | 12/1990 | Higson et al. | 128/200.18 |
| 5,198,157 | A * | 3/1993 | Bechet | 264/9 |
| 5,516,043 | A * | 5/1996 | Manna et al. | 239/102.2 |
| 5,642,570 | A | 7/1997 | Lee | |
| 6,311,903 | B1 | 11/2001 | Gaw et al. | |
| 6,679,436 | B1 | 1/2004 | Onishi et al. | |
| 6,814,071 | B2 * | 11/2004 | Klimowicz et al. | 128/200.16 |
| 6,863,224 | B2 * | 3/2005 | Terada et al. | 239/102.1 |
| 6,866,212 | B2 * | 3/2005 | Sumiyoshi et al. | 239/690 |
| 7,108,197 | B2 * | 9/2006 | Ivri | 239/4 |
| 7,614,572 | B2 * | 11/2009 | Yamaguchi et al. | 239/690 |
| 7,878,991 | B2 * | 2/2011 | Babaev | 601/2 |
| 2003/0088911 | A1 | 5/2003 | Gedouin | |
| 2003/0164417 | A1 | 9/2003 | Balachandran et al. | |
| 2004/0251314 | A1 | 12/2004 | Schramm et al. | |
| 2004/0256487 | A1 * | 12/2004 | Collins et al. | 239/338 |
| 2005/0279854 | A1 | 12/2005 | Martens et al. | |
| 2006/0064892 | A1 | 3/2006 | Matsui et al. | |
| 2007/0120898 | A1 * | 5/2007 | Lu et al. | 347/69 |
| 2007/0158459 | A1 * | 7/2007 | Aval et al. | 239/102.1 |
| 2007/0176017 | A1 * | 8/2007 | Berger et al. | 239/102.2 |
| 2008/0051693 | A1 * | 2/2008 | Babaev | 604/22 |
| 2008/0135643 | A1 | 6/2008 | Cohen et al. | |
| 2008/0223953 | A1 | 9/2008 | Tomono et al. | |
| 2008/0265055 | A1 | 10/2008 | Quan et al. | |
| 2008/0277495 | A1 | 11/2008 | Duru | |
| 2009/0056009 | A1 | 3/2009 | Matsubara et al. | |
| 2009/0200392 | A1 | 8/2009 | Duru et al. | |
| 2009/0200394 | A1 * | 8/2009 | Babaev | 239/102.1 |
| 2009/0200398 | A1 | 8/2009 | Duru et al. | |

FOREIGN PATENT DOCUMENTS

| | | | |
|---|---|---|---|
| DE | 32 02 597 | A1 | 8/1983 |
| EP | 0 389 665 | A1 | 10/1990 |
| EP | 0 569 611 | A1 | 11/1993 |
| EP | 1 435 209 | A1 | 7/2004 |
| EP | 1 508 382 | A1 | 2/2005 |
| FR | 1.471.557 | A | 3/1967 |
| FR | 2 532 861 | A1 | 3/1984 |
| FR | 2 747 542 | A3 | 10/1997 |
| FR | 2 780 664 | A1 | 1/2000 |
| JP | 3-4954 | A | 1/1991 |
| JP | 4-110057 | A | 4/1992 |
| JP | 10-85314 | A | 4/1998 |
| WO | WO 2004085079 | A1 * | 10/2004 |
| WO | WO 2006109364 | A1 | 10/2006 |
| WO | WO 2007/104859 | A1 | 9/2007 |

OTHER PUBLICATIONS

French Search Report from French Application No. FR 08 50927 filed Feb. 13, 2008.

French Search Report from French Application No. FR 08 50926 filed Feb. 13, 2008.

Co-pending U.S. Appl. No. 12/370,096, filed Feb. 12, 2009.

Co-pending U.S. Appl. No. 12/370,321, filed Feb. 12, 2009.

Office Action dated Mar. 29, 2012 from co-pending U.S. Appl. No. 12/370,321.

Response dated Jun. 29, 2012 from co-pending U.S. Appl. No. 12/370,321.

Office Action dated Jul. 22, 2011 from co-pending U.S. Appl. No. 12/370,096.

Office Action dated Oct. 19, 2011 from co-pending U.S. Appl. No. 12/370,321.

Response dated May 16, 2011 from co-pending U.S. Appl. No. 12/370,096.

Response dated Dec. 22, 2011 from co-pending U.S. Appl. No. 12/370,096.

Response dated Jul. 29, 2011 from co-pending U.S. Appl. No. 12/370,321.

Response dated Jan. 19, 2012 from co-pending U.S. Appl. No. 12/370,321.

Office Action dated Feb. 15, 2011 from co-pending U.S. Appl. No. 12/370,096.

Office Action dated Mar. 29, 2011 from co-pending U.S. Appl. No. 12/370,321.

* cited by examiner

SPRAY HEAD INCLUDING A SONOTRODE

This application claims the benefits of priority of French Application No. 08 50927 filed on Feb. 13, 2008 and U.S. Provisional Application No. 61/033,332 filed on Mar. 3, 2008, which is incorporated by reference herein.

This application is related to U.S. patent application Ser. No. 12/370,321, entitled "A Device for Spraying A Cosmetic Composition While Blowing Hot or Cold Air", and U.S. patent application Ser. No. 12/370,096, entitled "A Spray Head Including A Sonotrode With A Composition Feed Channel Passing Therethrough", each filed concurrently herewith. The contents of these related applications are explicitly incorporated by reference.

FIELD OF THE PRESENT DISCLOSURE

The present disclosure relates to devices for spraying a composition, in particular for spraying a composition on keratinous material such as, for example, human skin or hair.

The present disclosure relates more particularly to a spray head including a sonotrode, also referred to as an acoustic amplifier, for transmitting ultrasound vibration from a vibration-generating transducer, also known as a generator, to an ejection surface for ejecting particles of a composition.

The sonotrode may be placed in an air stream for conveying the particles of composition onto the region for treatment.

BACKGROUND OF THE PRESENT DISCLOSURE

Spray devices including a sonotrode have already been proposed. By way of example, U.S. Pat. No. 3,970,250 and European patent applications Nos. EP 0 389 665 and EP 1 508 382 A1 disclose spray heads having composition feed channels passing therethrough that are of constant cross-section, and that open out to the front face of an end collar of the sonotrode, said front face defining the ejection surface.

In U.S. Pat. No. 3,970,250, the sonotrode has a frustoconical portion that connects directly with the end collar. The sonotrode is placed inside a nozzle for blowing air, being set back from the opening through which air leaves the nozzle. The sonotrode is fastened via a vibration node of the frustoconical portion. The nozzle has a converging portion that passes close to the free edge of the collar, thereby reducing the flow section available to the air stream and, according to that patent, preventing the composition from flowing over the rear face of the collar.

Application No. EP 0 389 665 A1 discloses a shutter disposed in such a manner that in the absence of spraying, it closes the orifice through which the composition feed channel opens out into the ejection surface. The shutter is controlled by a rod that passes through the sonotrode via the feed channel. Such a device is of relatively complex construction and may result in added time and cost.

In application No. EP 1 508 382 A1, an end collar is pierced by multiple orifices for passing an air stream for entraining particles of a composition. Composition feed takes place by bringing the composition directly onto the ejection surface via a duct external to the sonotrode.

EP 0 569 611 A1 discloses a spray device including a peristaltic pump for bringing the composition onto the ejection surface.

Application WO 2007/104859 A1 discloses a device in which the composition is brought into contact with the ejection surface by a capillary wick. The sonotrode includes an end collar that is connected to a circularly-cylindrical portion. The use of a capillary wick may not enable compositions that are relatively viscous to be sprayed. The collar may not bend under the effect of the sonotrode vibrating.

FR 2 747 542 discloses a hair dryer arranged to spray a mist of fine water droplets in order to humidify the hair.

FR 2 532 861 describes an ultrasound sprayer for operating at a frequency of about 60 kilohertz (kHz), in particular for a fuel oil burner. The thickness of the end collar is about 1 millimeter (mm) for a diameter of about 12 mm.

U.S. Pat. No. 4,541,564 discloses a high flow rate spray device. The thickness of the end collar is about 3 mm for a diameter about 5 centimeters (cm), thereby making the spray device relatively bulky.

U.S. Pat. No. 3,904,896 discloses a spray device having an end plate with a diameter of 10 mm for a thickness of 1 mm.

Therefore, it is desirable to overcome one or more of the disadvantages of the prior art with a sprayer which meets one or more of the following desires:

- firstly the spray should be precise and as uniform as possible so as to facilitate the spraying operation and, where desired, so as to enable makeup to be applied regularly. In particular, it may be found desirable for the spot formed by the sprayed composition to have limited or no marked central void, associated with the presence of the sonotrode in the vector air stream;
- the size of the spray droplets should substantially satisfy health standards, minimizing fine droplets;
- the flow rate of the composition should be sufficient to ensure that the spraying operation is not too lengthy and/or uncomfortable;
- the spray device should be capable of adapting to compositions presenting viscosities that may vary with varying formulations;
- the device should be ergonomic, with sufficient operating lifetime, easy to handle, and reliable;
- the spray head should not clog easily and, where appropriate the spray should, need be easy to clean;
- operation should take place without the device clogging without an excessive and undesired accumulation of composition in zones of the device; and
- the cost of the device should remain compatible with mass distribution to the public.

OBJECT AND BRIEF SUMMARY OF THE PRESENT DISCLOSURE

The present disclosure seeks to further improve spray devices for spraying a composition, in particular spraying onto human keratinous material.

Exemplary embodiments of the present disclosure provide a device for spraying a cosmetic composition, the device including a sonotrode, the sonotrode having an end collar defining an ejection surface for ejecting particles of composition, the collar being suitable for bending under the effect of vibration of the sonotrode.

The present disclosure may make it possible to obtain a spray that gives rise to satisfactory results.

The present disclosure may make it possible in particular to obtain relatively high spraying efficiency.

While oscillating the collar may be deformed by changing the shape of the ejection surface, which may for example pass from being a plane at rest to being concave or convex towards the front. The amplitude of bending towards the front or towards the rear may be greater than or equal to 5 micrometers (μm) from the rest position, e.g., lying in the range 5 μm to 25 μm relative to the rest position, giving a total amplitude of 10 μm to 50 μm.

The minimum thickness of the end collar in the region where particles of composition are ejected may, for example, lie in the range 0.4 mm to 0.6 mm, in the range 0.45 mm to 0.55 mm, or approximately equal to 0.5 mm.

Droplets of composition may be ejected over the entire circumference of the end collar, thereby contributing to obtaining a spray that is substantially uniform.

Other exemplary embodiments of the present disclosure also provide a device for spraying a cosmetic or dermatological composition, the device comprising a sonotrode and a transducer coupled to the sonotrode, the sonotrode presenting an end collar defining an ejection surface for projecting particles of composition, the sonotrode also including a portion of decreasing diameter that is extended by a cylindrical portion (or "ejector") that is connected to the end collar, the ratio of the transducer diameter divided by the diameter of the cylindrical portion being less than or equal to 4.5, for example, 4 or 3.7, and possibly greater than or equal to 3. In some embodiments, lying in the range 3.5 to 3.7; and/or the ratio of the collar diameter divided by the diameter of the cylindrical portion lying in the range 7/6 to 13/4; and/or the ratio of the diameter of the collar divided by the thickness of the collar lying in the range 70/6, e.g., 12, to 130/4, e.g., 32. The thickness of the collar may be no greater than 0.5 mm. Values of the ratio collar diameter/collar thickness greater than or equal to 15 and of collar thickness no greater than 0.5 mm may be desirable for good spraying.

These geometrical characteristics may lead to results that are particularly satisfactory. The collar may extend along a plane perpendicular to a longitudinal axis of the sonotrode.

The collar may have a transverse dimension that is less than or equal to λ/4, where λ is the wavelength of an ultrasound wave associated with the vibration in a material comprising the sonotrode.

The length of the sonotrode between the face of the sonotrode in contact with a transducer for setting the sonotrode into vibration and the ejection surface may be less than or equal to λ, e.g., of the order of λ/2.

The sonotrode may include a composition feed channel, and the composition feed channel may present a narrow portion.

The narrow portion may serve to brake the flow of composition and improve the performance of spraying. The narrow portion may in particular enable a relatively uniform spray to be obtained.

The presence of the narrow portion may result in easier fabrication of the remainder of the channel, which may be of relatively large section. Such a design may assist in limiting head losses.

The narrow portion may provide a certain amount of capillary retention when the device is not in use, thereby enabling exchange with air to be reduced. The use of a shutter for the feed channel can thus be avoided.

The present disclosure may be applied to numerous cosmetic or dermatological compositions, for example, a foundation, a self-tanning agent, a lotion for the body or the face, a composition containing a hair agent, and/or a sunscreen composition, among others.

The term "hair agent" is used to mean any ingredient for a composition that serves to provide cohesion to a piece of hair by depositing a material that limits relative movement between individual hairs for example any polymer.

It is possible to use any hair agent and it is also possible to use mixtures containing a plurality of such agents.

Conventionally, a distinction is drawn between hair agents that are cationic, anionic, amphoteric, or non-ionic.

The hair agent may be selected from silicone or non-silicone polyurethanes, linear sulfonic polyesters, acrylic copolymers with branched blocks, and octalacrylamide-acrylate-butylaminoethylmethacrylate copolymers among others.

Thus, exemplary hair agents may include, for example, Amphomer from National Starch, Luviset Si Pur from BASF, Fixate T100 from Noveon, Mexomere PW from Chimex, and AS 55S from Eastman.

The sprayed composition may have viscosity greater than or equal to 0.1 millipascal seconds (mPa·s), greater than or equal to 1 mPa·s, a range of about 10 mPa·s to 500 mPa·s, and in particular in the range 20 mPa·s to 150 mPa·s or 50 mPa·s to 100 mPa·s.

With a composition such as an oil, for example, viscosity may be measured at 25° C. with a Haake RS 600 imposed stress rheometer, as sold by the supplier Thermo Rhéo, fitted with a moving body of cone/plane shape of the 60/1° type (60 mm for an angle of 1°). Rising stress is imposed going from 0 to 1000 Pa over 100 seconds (s). Then the rheogram representing variation in viscosity as a function of shear rate may be plotted. The rheogram presents a plateau at low values for shear rate (known as the Newtonian plateau), said plateau corresponding to a stable value for viscosity and constituting the viscosity of the composition as determined in this way.

With a composition such as a foundation, for example, viscosity can be measured at 25° C. with a Rhéomat 180 viscosity meter fitted with the MK-R2 moving body and the MB-R2 measuring flask having a volume of 60 milliliters (mL) at a speed of rotation of 200 revolutions per minute (rpm), the measurement being performed after 10 minutes of rotation (after which time the viscosity is observed to stabilize, as is the speed of rotation of the moving body).

The sonotrode is coupled to a transducer that enables electrical energy to be transformed into ultrasound vibration. The resonant frequency of the sonotrode may be similar to that of the transducer. Coupling may be achieved, for example, by adhesive bonding or by screw fastening, and/or any other suitable fastening method.

The particles of composition are advantageously entrained towards the region for treatment by a stream of air, which may be produced, for example, by at least one airflow generator. By way of example, the flow rate of the air may lie in the range 4 cubic meters per hour ($m^3/h$) to 7 $m^3/h$, and in some embodiments in the range 5.5 $m^3/h$ to 6.5 $m^3/h$.

In some embodiments, the narrow portion may open out to the ejection surface. The narrow portion may present a cross-section that is constant over a distance of at least 1 mm and less than or equal to 10 mm. A length of the narrow portion may, for example, be less than equal to 7 mm, in the range 1 mm to 5 mm, e.g., 2.5 mm. The narrow portion may present a cross-section that is constant from the end where it opens out into the ejection surface to its opposite end.

The narrow portion presents a cross-section that is circular, which may lead to easier manufacture.

The channel may present a cross-section that is circular over its entire length.

The channel may be rectilinear, having substantially the same longitudinal axis as the sonotrode. The narrow portion may present a small cross-section that is less than or equal to 0.8 square millimeters ($mm^2$). In particular, the narrow portion may present a diameter less than or equal to 1 mm, e.g., lying in the range 0.4 mm to 0.8 mm, and is may be close to 0.6 mm.

In some embodiments, the channel may present a maximum cross-sectional area that is greater than or equal to 0.8 $mm^2$.

Outside the narrow portion, the channel may present a diameter lying in the range 1 mm to 2 mm, e.g., being close to 1.5 mm, or greater in some embodiments, in particular, when the transducer is fastened to the sonotrode by bolting.

The ratio of the length of the narrow portion divided by the total length of the sonotrode channel may lie in the range 0.04 to 0.4.

The ratio of the greatest cross-sectional area of the channel divided by the narrowest cross-sectional area of the channel may lie in the range 1 to 25, in particular in the range 4 to 10, e.g., in the range 6 to 6.5.

In some embodiments, the channel may feed the ejection surface via a single outlet orifice, which may be situated in the center of the ejection surface.

The sonotrode may be made as a single piece with a connection endpiece for connection to a tube for feeding the channel with a composition. The feed tube may be, for example, a flexible hose, thus enabling the hose to be used within a peristaltic pump. The channel may also be connected to the feed duct in some other way, for example, by means of an endpiece inserted in the sonotrode.

The endpiece may pass through the transducer, which transducer may be annular in shape.

By way of example, the outside diameter of the end collar may lie in the ranges 7 mm to 13 mm, 8 mm to 12 mm, 9 mm to 11 mm, and may be close to 10 mm. Embodiments with a diameter of 10 mm for the end collar and a minimum thickness of 0.5 mm for the collar, at a frequency of 100 kHz±10% may be desirable.

The peripheral annular region of the collar where the thickness of the collar is relatively small, and in particular less than or equal to 0.6 mm, may itself present a width, measured radially, that is greater than or equal to 0.2 mm, e.g., lying in the range 0.2 mm to 2 mm.

The end collar may present an annular area having a thickness of 0.5 mm that extends over a radially-measured width of at least 0.5 mm.

The sonotrode may present a portion of outside cross-section that decreases towards the ejection surface, and in particular a portion that is frustoconical. The angle at the apex of this frustoconical portion may lie in the range 10° to 45°, and may in particular be 30°.

The sonotrode may present a portion that is circularly cylindrical, as mentioned above. The portion of tapering for an outside section may join said circularly-cylindrical portion, the circularly-cylindrical portion being intermediate between the portion of tapering section, in particular of the frustoconical section, and the end collar.

The outside diameter of the circularly-cylindrical portion lies for example in the range 4 mm to 7 mm, and in particular, may be close to 5.5 mm.

The width of the circularly-cylindrical portion may lie for example, in the range 3 mm to 5 mm.

The lengths of the various portions of the sonotrode may be selected as a function of the nominal frequency at which the sonotrode is designed to resonate. Further, the ejection surface may be situated level with a vibration antinode. The distance between the ejection face and the transducer, and also the diameter of the end collar may depend on the wavelength λ, which equals c/f where c is the speed of sound in the material at the utilization temperature, and f is the frequency.

The sonotrode may be machined, preferably being made of metal, and may comprise aluminum or aluminum alloy, and/or titanium or titanium alloy, and/or stainless steel, e.g., 316 type stainless steel.

The excitation frequency of the transducer may lie for example, in the range 30 kHz to 200 kHz. By way of example, the excitation frequency may be of the order of 100 kHz±10%.

The mean size of the particles of the spray may depend on the frequency and on the rheological characteristics of the fluid that is to be nebulized among other things. In an exemplary embodiment of the present disclosure, the mean size of the particles may lie in the range 20 μm to 25 μm, in particular at a frequency of 100 kHz. The content of fine particles of size smaller than 10 μm may be less than 10% by volume.

Other exemplary embodiments of the present disclosure also provide a device for packaging and spraying a cosmetic or dermatological composition, and including a head as defined above.

The device may include a container containing the composition for spraying. The composition may be a care product or makeup among others, and in particular may be foundation or a composition including a hair agent, a self-tanning agent, and/or a sunscreen.

The container may be in the form of a removable cartridge.

The composition may be contained in a flexible pouch.

The device may include a box having a housing for receiving said cartridge, in particular a housing in its top portion.

The stream of air directed towards the keratinous material may be heated or cooled, depending on, for example, a fluid to be sprayed, ambient temperature, etc.

In some exemplary embodiments of the present disclosure, spraying may be triggered by the user acting on a control member, such as a pushbutton, for example.

Once a spray cycle has been triggered, a spray sequence having the following steps may take place:

i) switching on a airflow generator to create a stream of air for entraining particles of composition;

ii) after a predefined delay, setting the sonotrode into vibration by means of a transducer; and iii) after another delay, switching on a pump feeding the sonotrode with composition.

At the end of the spray cycle, the device may be stopped by successively stopping the pump, stopping the transducer, and stopping the airflow generator.

Other exemplary embodiments of the present disclosure also provide a spray device comprising a nozzle, a support plate inside the nozzle, a sonotrode coupled to a transducer and fastened to the support by snap-fastening, and a gasket interposed between a shoulder of the support and a shoulder of the sonotrode.

This may make it easier to mount the sonotrode in the device.

Other exemplary embodiments of the present disclosure may also provide a spray device comprising a sonotrode, a transducer of annular shape coupled to the sonotrode, the sonotrode being made as a single piece with an endpiece into which a tube is inserted for feeding the composition for spraying. This facilitates construction of the device.

Other exemplary embodiments of the present disclosure may also provide a cosmetic treatment method e.g., of the skin, in particular a makeup method or a method of treating the hair, the method including the step of:

spraying a cosmetic composition onto the human keratinous material concerned, by using a spray head as defined above.

BRIEF DESCRIPTION OF THE DRAWINGS

The present disclosure can be better understood on reading the following detailed description of exemplary non-limiting embodiments thereof, and on examining the accompanying drawings, in which.

MORE DETAILED DESCRIPTION

Figure 1:
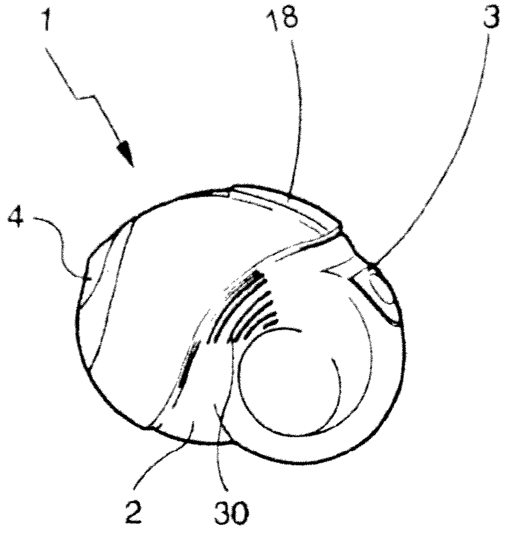
FIG. 1 is a diagrammatic elevation view showing an exemplary spray device made in accordance with some embodiments of the present disclosure.
Figure 2:
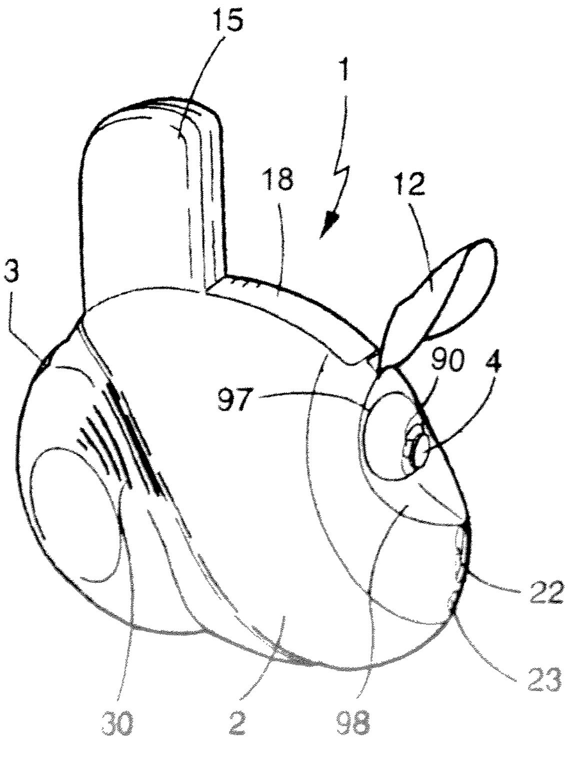
FIG. 2 shows the device of FIG. 1 with an exemplary cartridge of composition in place, ready for spraying.
Figure 3:
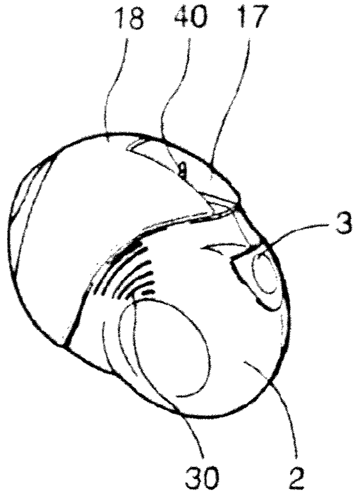
FIG. 3 shows the device of FIG. 1 with an exemplary access hatch to the cartridge-receiver housing open, ready for the cartridge to be put into place on the housing.

Spray device 1 shown in FIGS. 1 to 3 includes a box 2 suitable for handling by the user to spray a composition onto the skin or onto other human keratinous materials, such as the lips and/or the hair, for example.

Box 2 in the example shown has a pushbutton 3 enabling the user to trigger spraying by pressing or otherwise actuating pushbutton 3. In a variant, pushbutton 3 could be situated elsewhere, and it could be replaced by a trigger or a touch-sensitive switch, among other things, for example.

At the front, and as can be seen in FIG. 2 in particular, the device includes a surface 4 for ejecting particles of the composition. In some embodiments, this surface may be directed towards a region that is to be treated so as to enable the particles of composition to become deposited on said region.

In the example described, box 2 includes a protective cover 12 suitable for folding down over the ejection surface 4 when not in use. By way of example, cover 12 is hinged to the body of box 2 to be movable between a lowered position in which it covers ejection surface 4 and a raised position. In a variant embodiment, box 2 may not have a protective cover or cover 12 is mounted on box 2 in some other way.

When in the down position, cover 12 may extend so as to continue to the outside surface of box 2.

Box 2 may receive a cartridge 15 containing the substance for spraying, cartridge 15 being inserted in a housing 17 in box 2. Cartridge 15 may be removable, fixed, or of any suitable configuration As can be seen in FIG. 1, while not in use, housing 17 may be shut by a shutter flap 18.

In the example shown, housing 17 opens in an upward direction.

Shutter flap 18 may be mounted to slide on box 2. In some alternative embodiments, housing 17 may be positioned otherwise in box 2.

By way of example, the composition contained in cartridge 15 may be for example: a foundation; a self-tanning agent; a lotion for the body or the face, and/or a composition containing a hair agent.

By way of example, the capacity of cartridge 15 may lie in the ranges 1 mL to 100 mL, 5 mL to 20 mL, and in particular may be 10 mL.

In some embodiments, device 1 may receive a plurality of cartridges 15 containing different compositions or a cartridge 15 containing a plurality of compositions, with means for selecting which composition is to be sprayed. In some embodiments means for adjusting the proportion of one composition relative to another in a sprayed mixture may be included. Where desired, a single cartridge 15 may contain a plurality of compositions together with selector means for selecting which composition is to be sprayed and/or for adjusting the proportions of the various compositions in the sprayed mixture.

In the example described, box 2 may include a general on/off switch 22 and an indicator light 23 to show when it is in operation. On its sides, box 2 may include air inlets 30.

Figure 4:
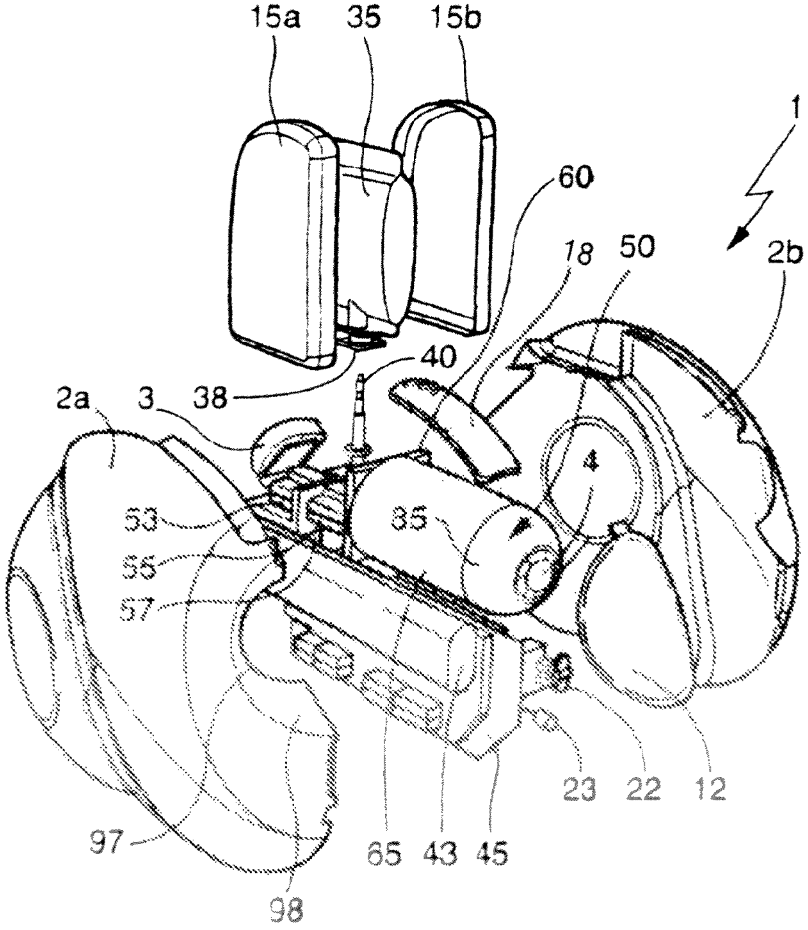
FIG. 4 is a diagrammatic and fragmentary exploded perspective view showing the device of FIGS. 1 to 3.

FIG. 4 shows that the body of box 2 may be formed by assembling together two half-shells **2*a* and 2*b*. By way of example, half-shells 2*a* and 2*b* may be mounted together as a tight-fit, possibly releasably, e.g., being snap-fastened to one another and/or held together by one or more screws. In some embodiments, these half-shells 2*a* and 2*b*** may be made by molding a thermoplastic material, for example.

Cartridge 15 may comprise two half-shells **15*a* and 15*b* that are united around a flexible pouch 35 containing the composition for spraying. By way of example, flexible pouch 35 may be heat-sealed onto a coupling endpiece 38 for engaging a suction endpiece 40 present in the housing 17**. Under such circumstances, these endpieces may engage each other so as to define a releasable connection, e.g., of the male/female type.

The use of flexible pouch 35 may enable the composition to be taken without air being drawn into flexible pouch 35. In some embodiments, cartridge 15 may contain a reservoir other than a flexible pouch, e.g., a reservoir with a movable end wall.

In a variant embodiment, cartridge 15 may include a visible indicator showing the extent to which it has been emptied, e.g., a transparent window made in one of half-shells **15*a* and/or 15*b* and/or in flexible pouch 35**.

By way of example, half-shells **15*a* and 15*b*** may be mounted as a tight-fit, possibly separably, e.g., being snap-fastened and/or adhesively bonded one on the other, or fastened in some other way, e.g., being made of a thermoplastic material that may be opaque or transparent.

Placing cartridge 15 in the top portion of the device may make it possible to benefit from a gravity effect for feeding the composition.

Where appropriate, cartridge 15 may be replaced by a cartridge containing a cleaning solution, for the purpose of cleaning the device, in particular the sonotrode and the ejection surface.

The device may be proposed to the user together with one or more cartridges 15 containing one or more compositions for spraying and the above-mentioned cleaner cartridge, for example within a common package.

The cleaner cartridge may optionally be refillable.

The cleaning solution may be selected from one of the solvents of the cosmetic composition in order to be compatible therewith, and for example it may comprise isododecane, a volatile silicone, and/or alcohol and/or water.

Where appropriate, the device may include a cartridge-recognition system, e.g., using an electromechanical feeler or electrical contacts or a radiofrequency identification (RFID) chip or any other suitable device.

By knowing the content of cartridge 15 that is in position, device 1 may be enabled to adapt its operating parameters automatically to the composition for spraying, e.g., in terms of delivery rate, excitation frequency, air flow rate, and/or air temperature, where appropriate.

Box 2 may house an energy source 43, e.g., one or more optionally-rechargeable batteries, together with a printed circuit 45 carrying the electronic components of device 1. These components serve to generate the voltage utilited for spraying, and to control the various electrical elements. They may also perform auxiliary functions such as, for example: calculating the quantity of composition that remains available for spraying, for example, for the purpose of warning the user when it is necessary to replace cartridge 15.

In order to replace the battery, it may be necessary to open box 2 by separating its half-shells 2*a* and 2*b*. In some embodiments, access to the battery compartment may be obtained without opening the box, via an access hatch to said compartment. Where appropriate, spray device 1 may include an electrical connector enabling a rechargeable battery present in the box to be recharged.

Box 2 also houses a spray assembly (or "head") 50 together with a pump 53, pump 53 being connected firstly to the suction endpiece 40 and secondly to the spray assembly 50 by means of a tube 55, which is preferably a flexible hose.

By way of example, pump 53 may be of the peristaltic type, comprising an electric motor 57 turning one or more wheels that bear against tube 55 so as to urge the composition towards spray assembly 50. The delivery rate of the composition while pump 53 is in operation may lie for example in the range 0.5 grams per minute (g/min) to 2 g/min.

Where desired, the delivery rate may be adjustable by the user over certain preset values.

In some embodiments, other types of pumps may be used, for example: gear, diaphragm, and/or piston pumps. It is also possible to use a gravity feed or a resilient shrinkable pouch.

Figure 5:
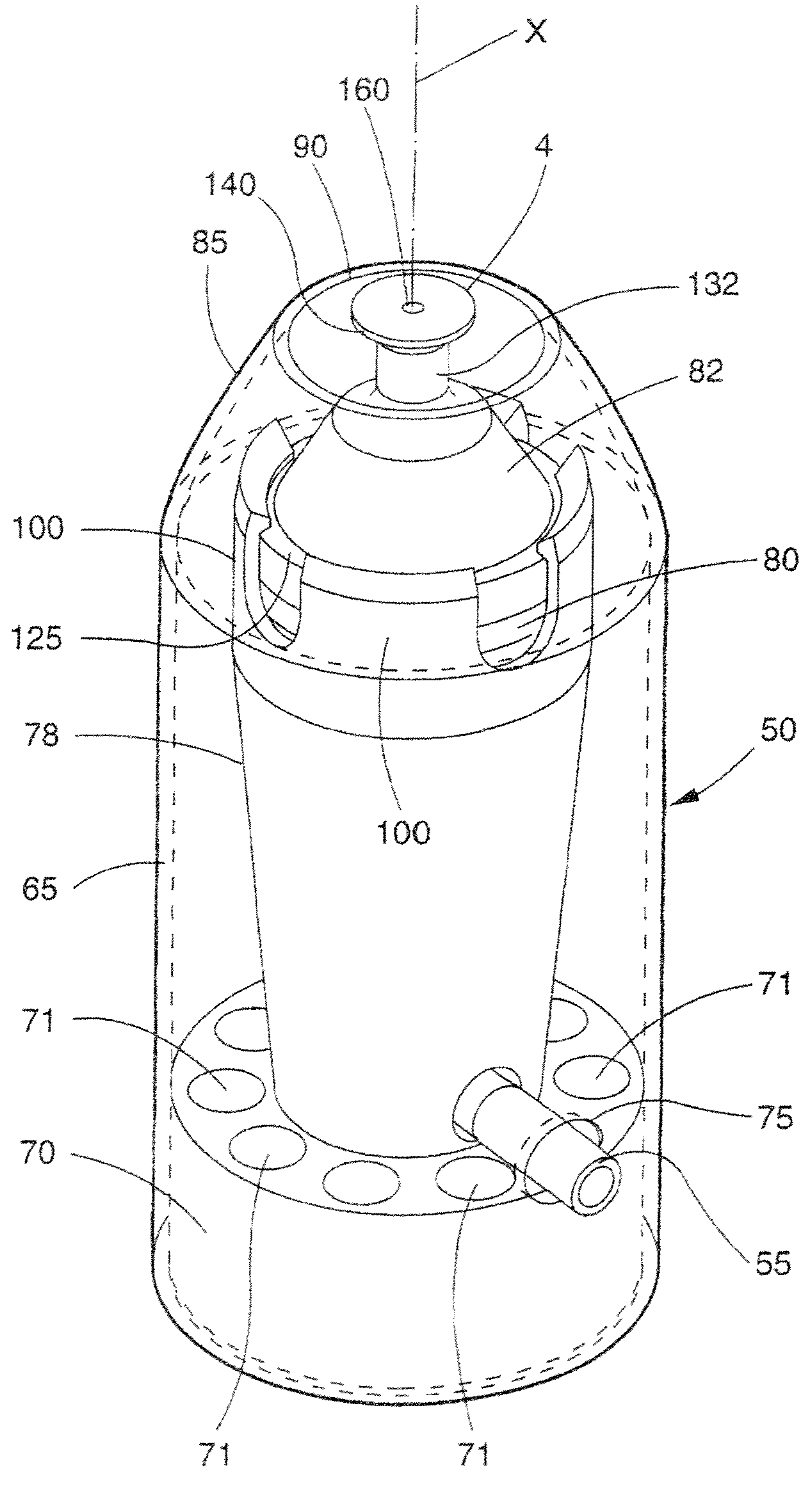
FIG. 5 is a diagrammatic and fragmentary perspective view of an exemplary sprayer assembly according to some embodiments of the present disclosure.

At the rear, the spray assembly 50 includes a airflow generator 60 (e.g., a fan, compressed air, etc.) as can be seen in FIG. 4, the airflow generator 60 not being shown in FIG. 5 in order to clarify the drawing.

The spray assembly 50 may also include a nozzle 65 comprising a tubular body that is closed at the rear by a stopper 70 having openings 71 for passing air blown by the airflow generator 60.

By way of example, the airflow generator 60 may include a fan, compressed air, and/or any other suitable device, and may be fastened to the stopper 70, e.g., by one or more screws.

By way of example, the axis of rotation of the airflow generator may coincide with the longitudinal axis of the nozzle 65.

The rate at which the airflow generator 60 ejects air into the nozzle 65 may lie in the range 4 $m^3/h$ to 7 $m^3/h$, for example.

The airflow generator 60 may draw in air from outside box 2 through inlets 30 among others.

The airflow generator 60 may operate continuously once the user has switched device 1 on by means of general switch 22, or in some embodiments only when the user triggers spraying by pressing on pushbutton 3. In an example, the operation of airflow generator 60 may continue after the end of spraying for a predefined duration or until the user acts again on device 1, thereby enabling the user to take advantage of the air being blown to accelerate drying of the composition that has been deposited on the region to be treated.

A spraying cycle controlled by acting on pushbutton 3 may comprise initially switching on airflow generator 60, and then after a delay lying in the range of 300 milliseconds (ms) to 800 ms, for example e.g. about 500 ms, the spray head may be excited. After another delay, e.g., lying in the range 300 ms to 800 ms, and in particular of about 500 ms, pump 53 may be switched on. Spraying may be stopped when pushbutton 3 is released, with the above-described steps following one another in the reverse order or other suitable orders/steps.

Device 1 may include heater means 200 for heating the air that is blown towards the surface being sprayed. This may be accelerate drying of the composition and result in device 1 being more comfortable in use. Heater means 200 can also heat the sonotrode and reduce the viscosity of the composition, thereby making it flow more easily and making it easier to spray.

Figure 6:
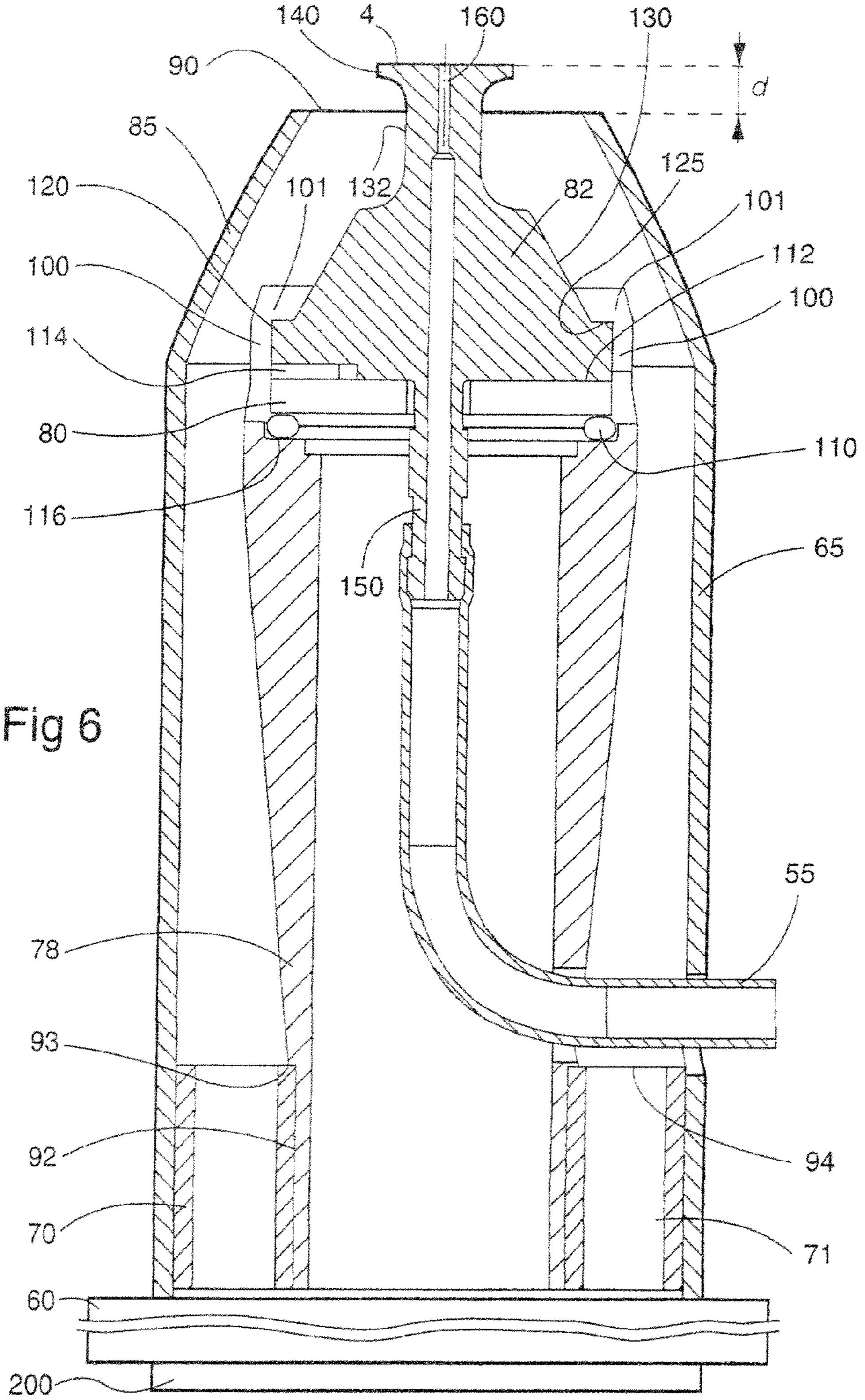
FIG. 6 is a diagrammatic and fragmentary longitudinal section view of the exemplary sprayer assembly of FIG. 5.
Figure 8:
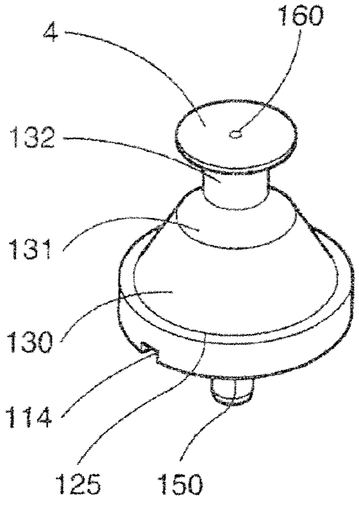
FIG. 8 shows an exemplary sonotrode of the sprayer in perspective and in isolation.
Figure 7:
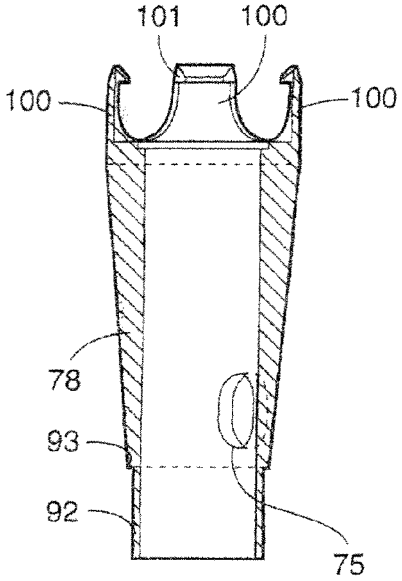
FIG. 7 shows an exemplary transducer support of the sprayer in isolation.
Figure 9:
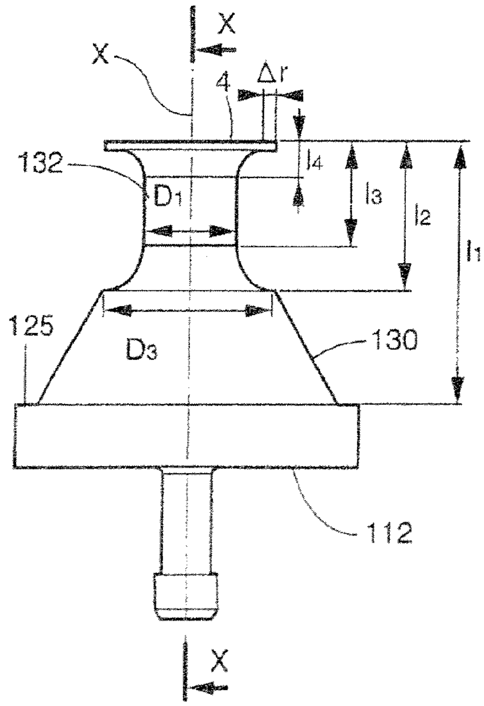
FIG. 9 is an elevation view of an exemplary sonotrode.

By way of example, heater means 200 may comprise an electric resistance heater 210 that can be incorporated in the airflow generator 60 or placed upstream or downstream therefrom, as shown in FIG. 6.

By way of example, heater means 200 may be fastened to the airflow generator 60.

Figure 13:
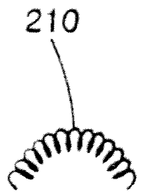
FIG. 13 is a diagrammatic perspective view of an exemplary resistance heater device.

In one example, resistance heater 210 may be constituted by a Nichrome wire with a diameter of 0.51 mm and a length of 2.8 meters (m), that is wound into the shape of a spring, as shown in FIG. 13. Resistance heater 210 may be placed behind the airflow generator 60, being fed with power, for example, 36 watts (W). Such a resistance heater 210 enables an air stream to be produced at a temperature of approximately 36° C. at 10 cm from the composition ejection surface.

Nozzle 65, airflow generator 60, and heater means 200 may be secured to one another prior to being assembled within box 2. Thus, these elements may constitute a one-piece assembly that may be easy to mount in box 2. Such elements may be disposed in alignment one behind another. In some embodiments, the alignment of these elements may make device 1 relatively compact.

By way of example, the temperature at which the hot air leaves the nozzle 65 may lie in the range 30° C. to 40° C., and may be about 37° C.

Where desired, the outlet temperature of the air may be regulated by having a temperature sensor present that is exposed to the hot air stream and that is associated with an electronic regulation loop.

Device 1 may be arranged so as to enable the user to select between operation in which the air blown by device 1 is heated and operation in which the air blown by the device is not heated.

By way of example, this selection may be made using a selector that may be actuated by the user, the selector being controlled by pressing to a greater or lesser extent on pushbutton 3 that triggers spraying, for example.

In an example, moderate pressure on pushbutton 3 may trigger spraying with air being blown at ambient pressure, while greater pressure may trigger spraying with hot air being blown.

Heater means 200 may switch on at substantially the same time as the airflow generator is switched on and it may switch off at substantially the same time likewise, or the respective switching of heater 200 and of airflow generator 60 may be different as desired.

Spray device 1 may be arranged to switch to a stand-by mode in the absence of action on pushbutton 3 for a predefined duration. Causing device 1 to return to normal operation may then occur once pressure is applied on pushbutton 3, or the general on/off switch 22 is operated, for example.

The body of nozzle 65 may be provided with a lateral opening 75 for passing a composition feed tube 55, and it may house a support 78 that may hold a piezoelectric transducer 80.

Transducer 80 may be mechanically coupled to a sonotrode 82 serving to amplify the electromechanical vibration of transducer 80, which vibration may be radial or longitudinal, so as to transmit the vibration to the ejection surface 4, which surface is defined by an end collar of the sonotrode 82.

In some embodiments, this surface may be machined in aluminum, but other materials could be used, in particular other metals or alloys.

The rear face of sonotrode 82 may be adhesively bonded to transducer 80, however it could be fastened in some other way, for example, by mechanical means such as screw fastening.

By way of example, the body of nozzle 65 is circularly cylindrical and it may be molded out of a thermoplastic material.

At the front, nozzle 65 may present a converging portion 85 terminating in an opening 90 on the same axis X as the axis of sonotrode 82. This opening 90 may be circular in the example described, with a diameter lying in the range 14 mm to 20 mm, e.g., of the order of 16 mm.

Converging portion 85 projects into a setback 98 in box 2, formed by assembling together half shells **2*a* and 2*b*, with the bottom of setback 98 defining an opening 97 that may locally match the outside section of nozzle 65**.

In the example shown, the stream of air blown by nozzle 65 may be not deflected by the remainder of box 2, where setback 98 presents sufficient width.

The air blown by airflow generator 60 may leave via the opening 90 to constitute a stream of air that is directed generally along the axis X.

As can be seen in FIG. 6 in particular, ejection surface 4 projects from the plane P of opening 90 by a distance d. The plane P of opening 90 may be substantially perpendicular to the axis X.

By way of example, the distance d may lie in the ranges 2 mm to 4 mm, 2 mm to 3 mm, or 2.2 mm to 2.9 mm. In particular opening 90 may have a diameter of about 16 mm. Such values may enable a relatively uniform spray to be obtained with little loss at a distance 5 cm or even 10 cm from ejection surface 4.

A distance d lying outside the above range can lead to the spray being less uniform, for example with a central void and/or leaving a spot of composition that is less precise.

By way of example, support 78 may be molded as a single piece of thermoplastic material, and it includes a portion 92 designed to engage as a force-fit in central opening 72 through stopper 70 until a shoulder 93 of support 78 comes into abutment against bottom face 94 of stopper 70.

At its end opposite from mounting portion 92, support 78 may have elastically-deformable tabs 100, e.g., four tabs, each provided with an end tooth 101 which may serve to hold sonotrode 82 and transducer 80 by snap-fastening, or other suitable methods, as shown in FIGS. 5 and 6.

In addition to holding sonotrode 82, support 78 may also contribute to achieving distribution of the air stream inside nozzle 65 around sonotrode 82.

In the example described, transducer 80, which may be annular in shape, may be sandwiched between an O-ring gasket 101 and rear face 112 of sonotrode 82.

A recess 114 is formed in rear face 112 for passing a first power supply wire to sonotrode 82, contacting the face of transducer 80 adjacent to sonotrode 82. Its other face may be electrically connected to a second power supply wire.

In the example described, apart from the recess 114, sonotrode 82 may be a body of revolution about the axis X.

Various different transducers may be used. A transducer 80 including a piezoelectric ceramic that is suitable for the present disclosure may be constituted, for example, by that sold by the supplier Ferroperm under the reference 26132. It comprises a PZ26 piezoelectric ceramic in the form of a ring having an outside diameter of 20 mm, an inside diameter of 3.8 mm, and a thickness of 2 mm.

O-ring 110 rests on a shoulder 116 of support 78, as can be seen in FIG. 6, and transducer 80 may bear via its face opposite from sonotrode 82 on the O-ring 110, close to its radially outer edge.

O-ring 110 may enable sonotrode 82 and the transducer 80 to be mounted substantially without clearance on support 78.

At its rear end, sonotrode 82 may include a first enlarged cylindrical segment 120 defining a shoulder 125 on which teeth 101 can catch.

Sonotrode 82 extends forwards beyond shoulder 125 in the form of a frustoconical portion 130 that is connected via a fillet 131 to a second cylindrical segment 132 about the axis X. This cylindrical segment 132 may be connected by a fillet 134 to an end collar 140 having a front face that is generally perpendicular to the axis X and that may define composition ejection surface 4.

The diameter D of first cylindrical segment 120 may lie for example, in the range 18 mm to 22 mm, e.g., 20 mm. By way of example, this diameter D may correspond substantially to the greatest diameter of transducer 80. In some embodiments, transducer 80 may present a diameter of 15 mm.

The length $l_0$ of cylindrical segment 120 may lie, for example, in the range 1.5 mm to 5.5 mm, for example equal to 3.5 mm.

The greatest diameter $D_2$ of frustoconical portion 130 may lie, for example, in the range 15.5 mm to 19.5 mm, and may, for example, be equal to 17.5 mm. The smallest diameter $D_3$ of frustoconical portion 130 may lie, for example, in the range 8 mm to 12 mm, and may, for example, be equal to 10 mm. An angle $\alpha$ at the apex of frustoconical portion 130 may be approximately 30°.

The radius of curvature of fillet 131 may lie, for example, in the range 2 mm to 3 mm and may be equal to 2.5 mm in the example shown, while the radius of curvature of fillet 134 may lie, for example, in the range 1 mm to 2 mm, and may be equal to 1.5 mm.

A distance $l_1$ between shoulder 125 and ejection surface 4, as measured along the axis X, may lie, for example, in the range 13 mm to 17 mm, and may be equal to 14.9 mm, for example.

A distance $l_2$ between the apex of frustoconical portion 130 and ejection surface 4 may lie, for example, in the range 7 mm to 10 mm and may be equal to 8.4 mm.

A distance $l_3$ between the rear end of second cylindrical segment 132 and ejection surface 4 may lie, for example, in the range 4 mm to 8 mm, and may be equal to 5.9 mm.

A distance $l_4$ between the front end of second cylindrical segment 132 and ejection surface 4 may lie, for example, in the range 1.5 mm to 2.5 mm, and may be equal to 2 mm.

A diameter $D_1$ of second cylindrical segment 132 may lie, for example, in the range 4 mm to 6 mm and may be equal to 3.5 mm, while a thickness e of end collar 140, as measured along the axis X close to its radially-outer edge, may lie for example, in the range 0.4 mm to 0.6 mm, and may be equal to 0.5 mm.

A diameter $D_7$ of the end collar may lie, for example, in the range 7 mm to 13 mm, and may be equal to 10 mm.

In some embodiments, the rear face of end collar 140 may terminate substantially perpendicularly to the axis X.

A thickness of the collar may be constant from its periphery over an annular range of width Δr, measured radially, and may lie in the range 0.2 mm to 2 mm, for example, equal to 0.5 mm.

A ratio $D_7/D_1$ may lie, for example, in the range 7/6 to 13/4 while the ratio $D_7/e$ may lie in the range 70/6 to 130.4, for example.

One of skill in the art will recognize that the present disclosure is not limited to the shape of end collar shown in the drawing and other shapes are possible, for example an elliptical shape, among others. Under such circumstances, the term "diameter" applies to the circle that circumscribes the collar.

In the example described, sonotrode 82 may be made with a rear endpiece 150 for connection to feed tube 55, the endpiece 150 being a single piece. For example, such fabrication may involve machining endpiece 150 together with the remainder of sonotrode 82. Tube 55 may be engaged as a force-fit on the endpiece 150, for example.

A composition feed channel 160 may pass through sonotrode 82 along the axis X. A first portion **160*a* of channel 160 may include a constant inside diameter from the bottom end 162 of endpiece 150 to a point 165 situated within second cylindrical segment 132, where said portion 160*a* may be connected to a narrow portion 160*b* via a frustoconical bore 160*c***.

In its largest diameter portion **160*a*, an inside diameter $D_5$ of channel 160 may lie, for example, in the range 1 mm to 3 mm and may be equal to 1.5 mm, while a diameter $D_6$ of the narrow portion 160*b*** may lie, for example, in the range 0.4 mm to 0.8 mm, and may be 0.6 mm.

The presence of largest diameter portion **160*a* may make it easier to machine channel 160 and may assist in reducing head loss. The presence of narrow portion 160*b*** may lead to performance that is improved in terms of the quality of the resulting spray.

A length $l_7$ of narrow portion **160*b***, as measured along the axis X, may lie, for example, in the range 2 mm to 5 mm, and may be equal to 3 mm, for example.

Transducer 80 may be excited at a frequency lying, for example, in the ranges 30 kHz to 200 kHz, and more particularly 60 kHz to 200 kHz. Pump 53 may deliver the composition for spraying to ejection surface 4 via channel 160 passing through sonotrode 82.

The excitation frequency of transducer 80 may be constant, or, alternatively, may be servo-controlled so as to maximize the amplitude of vibration at ejection surface 4 and maximize spraying effectiveness.

The electronic components of the device may comprise an electronic circuit that serves to perform this function in desired manner.

At the end of spraying, where appropriate, the operation of the pump 53 may include a reversal of the direction of rotation of the motor for a short period of time in order to cause backflow of the composition present in channel 160 and thereby reduce the risk of the composition drying and plugging channel 160.

When a voltage is applied to transducer 80 via its first and second power supply wires, transducer 80 may vibrate, and in some embodiments, vibrates radially relative to the axis X. Vibrations generated in this way may propagate with amplitude being amplified in sonotrode 82 until it reaches ejection surface 4, which itself vibrates axially in bending.

Under the effect of the vibration, end collar 140 may deform, and the oscillation of collar 140 causes droplets of composition to be ejected over its entire circumference.

The mean size of the droplets delivered may lie, for example, in the range 20 μm to 30 μm.

The droplets of ejected composition may be entrained by the stream of air leaving opening 90 towards the surface for treatment, and they reach this surface in the form of droplets.

The delivery rate of the composition may lie, for example, in the range 0.5 g/min to 10 g/min, depending on the viscosity of the composition to be sprayed.

In some embodiments, a device of the present disclosure may enable spraying of a spot of composition having a diameter of about 40 mm to be formed in uninterrupted and uniform manner on the region to be treated.

Figure 10:
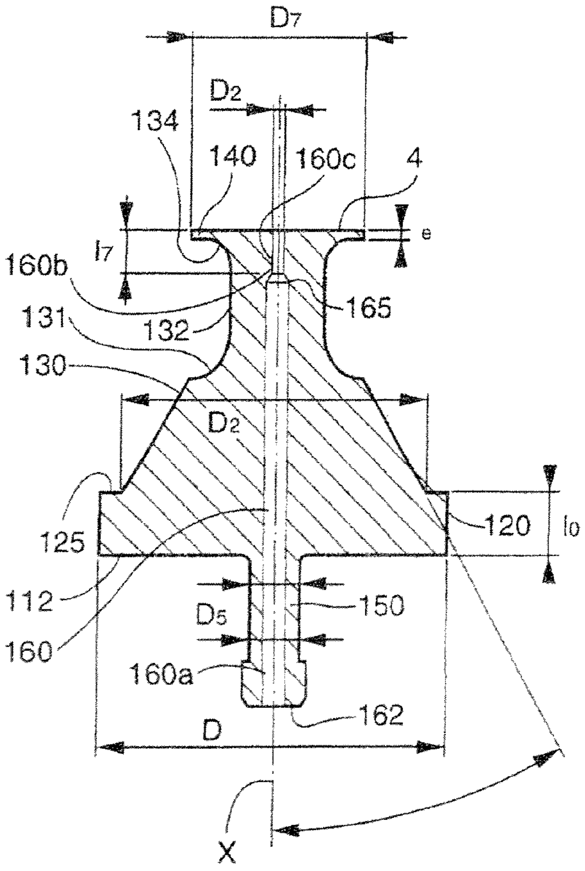
FIG. 10 is a longitudinal section of the exemplary sonotrode on X-X of FIG. 9.

In the example of FIG. 10, the particular values given for the dimensions of sonotrode 82 apply to a frequency $\underline{f}$ of 100 kHz.

For a different frequency f', the dimensions may be modified, on a first approach, by a factor f/f'.

Figure 11:
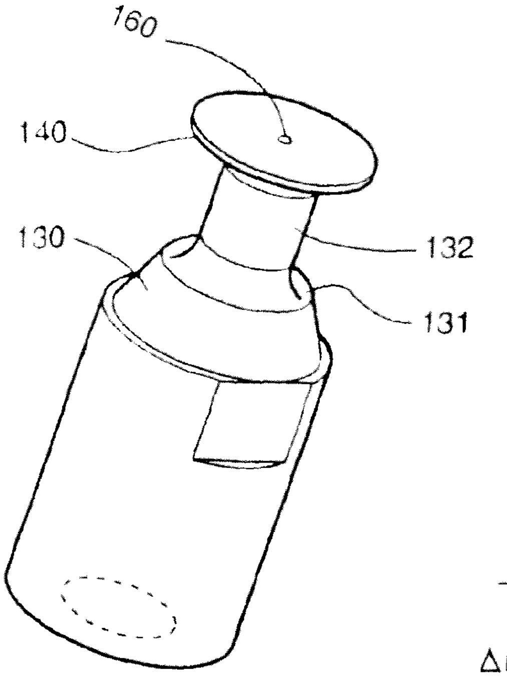
FIG. 11 is a perspective view of another embodiment of the sonotrode.
Figure 12:
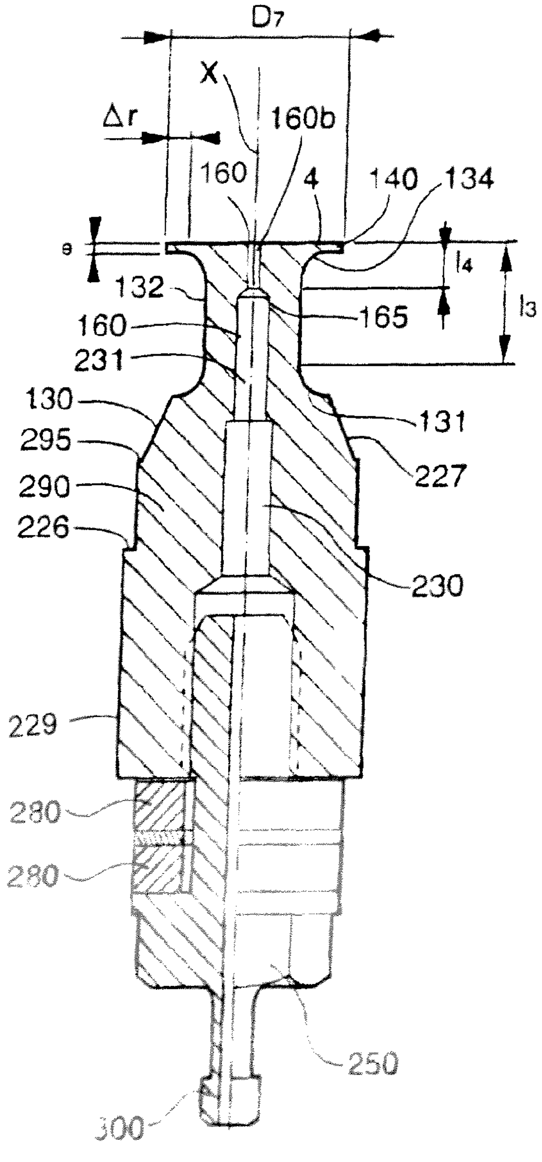
FIG. 12 is a diagrammatic and fragmentary longitudinal section view of a spray head including the sonotrode of FIG. 11.

FIG. 11 shows another embodiment of sonotrode 82 consistent with the present disclosure, and designed to operate a frequency of 60 kHz. This sonotrode 82 differs from that shown in FIG. 10 in its dimensions and in the shape of the body 290 situated behind the cylindrical portion 132.

In such an embodiment, sonotrode 82 may include an inside thread 220 that enables a vibration generator retention bolt 250 to be fastened, e.g., constituted by two piezoelectric ceramics 280 mounted opposite ways round.

A length $l_7$ of the narrow portion **160*c* may be 3.5 mm, for example. A length of cylindrical surface 225 from the end face opposite from collar 140 to a shoulder 226 of body 290 may equal approximately 18 mm, for example, and a distance of shoulder 226 to base 295 of a frustoconical portion 227 adjacent to the cylindrical portion 132** may, for example, be equal to 7 mm.

The housing 229 receiving the bolt 250 communicates with two successive bores 230 and 231 of respective decreasing diameters, e.g., respectively equal to 4 mm and 2.5 mm.

Bolt 250 may include a central opening enabling the composition for spraying to be delivered, and it may include an endpiece 300 for connection to tube 55.

One of skill in the art will recognize that the present disclosure is not limited to the embodiments described herein.

For example, in some embodiments, the composition may be fed via a needle that delivers the composition directly to the inside of sonotrode 82, set back from the composition outlet orifice.

The narrow portion of the channel may be formed by fitting a flow constrictor within sonotrode 82, such as for example a small sleeve forced into a channel of appropriate diameter in sonotrode 82.

Box 2 of device 1 may be of other shapes, in particular it may have the shape of a pen, for example.

Where appropriate, box 2 handled by the user may be connected via an electric cable to a base that includes at least one electrical power supply, e.g., a charging device.

In some embodiments, feed channel 160 may open out via a plurality of orifices onto ejection surface 4. These orifices may be disposed, for example, in an axially symmetrical configuration. The narrow portion of the channel may be situated upstream from channels communicating with the orifices, or in some embodiments, each branch of channel 160 leading to an orifice may include its own narrow portion.

Ejection surface 4 of sonotrode 82 may receive surface treatment, e.g., for the purpose of reducing its surface tension. For example it may receive a deposit of polytetrafluoroethylene (PTFE) or it may have a mirror polish, among other things.

Where appropriate, device 1 may be arranged to enable the projection d of ejection surface 4 relative to the opening 90 to be adjusted. This can improve focusing of the spray.

In some embodiments, device 1 may be used for spraying a composition into the atmosphere.

The term "comprising a" should be understood as being synonymous with "comprising at least one" unless specified to the contrary.

The value ranges should be understood as including the limit values, unless specified to the contrary.

Although the present disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

What is claimed is:

1. A device configured to spray either a cosmetic or a dermatological composition, the device comprising:

the cosmetic or dermatological composition;

a sonotrode;

a casing comprising a portion terminating in an opening defined by an external surface of the device; and an airflow generator configured to blow air via the opening, wherein the sonotrode comprises a composition feed channel and has an end collar defining an ejection surface for ejecting particles of the cosmetic or dermatological composition, the ejection surface projecting outside the device from the opening by a distance, wherein the end collar is bendable under the effect of vibration of the sonotrode and the ratio of a greatest diameter of the end collar divided by a thickness of the end collar ranges from 12 to 32, wherein the sonotrode comprises a portion of outside cross section that decreases towards the ejection surface, and wherein the composition feed channel feeds the ejection surface via a single outlet orifice and comprises a first diameter portion connected to a second diameter portion that is narrower than the first diameter portion and that opens out to the ejection surface at the outlet orifice.

2. A device according to claim 1, wherein the thickness of the end collar ranges from 0.45 mm to 0.55 mm.

3. A device according to claim 1, wherein the end collar comprises a circular outline.

4. A device according to claim 1, wherein a greatest diameter of the end collar ranges from 7 mm to 13 mm.

5. A device according to claim 1, wherein the ejection surface is planar at rest.

6. A device according to claim 1, wherein ejection of particles of the cosmetic or dermatological composition takes place over an entire circumference of the end collar.

7. A device according to claim 1, wherein a total amplitude of vibration of the ejection surface is greater than or equal to 10 μm.

8. A device according to claim 7, wherein the ejection surface is configured to vibrate by alternating between a concave shape and a convex shape.

9. A device according to claim 1, wherein a frequency associated with the vibration ranges from 30 kHz to 200 kHz.

10. A device according to claim 1, wherein the end collar includes a greatest transverse dimension that is less than or equal to $\lambda/4$, wherein $\lambda$ is a wavelength of an ultrasound wave associated with the vibration in a material comprising the sonotrode.

11. A device according to claim 10, wherein a length of the sonotrode between a face of the sonotrode in contact with a transducer coupled to the sonotrode, and the ejection surface is less than or equal to $\lambda$.

12. A device according to claim 1, wherein the sonotrode comprises aluminum.

13. A device according to claim 1, wherein a viscosity of the cosmetic or dermatological composition is greater than or equal to 0.1 mPa·s measured at 25° C.

14. A device according to claim 1, wherein a viscosity of the cosmetic or dermatological composition lies in a range of 10 mPa·s to 500 mPa·s measured at 25° C.

15. A device configured to spray either a cosmetic or a dermatological composition, the device comprising:

the cosmetic or dermatological composition;

a sonotrode, the sonotrode comprising a composition feed channel and an end collar defining an ejection surface for ejecting particles of the cosmetic or dermatological composition, the sonotrode comprising a portion of decreasing diameter extended by a cylindrical portion that is connected to the end collar, wherein the composition feed channel feeds the ejection surface via a single outlet orifice and comprises a first diameter portion connected to a second diameter portion that is narrower than the first diameter portion and that opens out to the ejection surface at the outlet orifice;

a transducer coupled to the sonotrode;

a casing comprising a portion terminating in an opening defined by an external surface of the device, the ejection surface projecting outside the device from the opening by a distance; and an airflow generator configured to blow air via the opening, wherein a first ratio comprising the transducer diameter divided by a diameter of the cylindrical portion ranges from 3 to 4.5, wherein a second ratio comprising a diameter of the end collar divided by the diameter of the cylindrical portion ranges from 7/6 to 13/4, and wherein a third ratio comprising the diameter of the end collar divided by a thickness of the end collar ranges from 70/6 to 130/4.

16. The device of claim 15, wherein the first ratio ranges from 3.5 to 3.7.

17. The device according to claim 1, wherein the distance the ejection surface projects outside the device from the opening ranges from 2 mm to 4 mm.

18. The device according to claim 15, wherein the distance the ejection surface projects outside the device from the opening ranges from 2 mm to 4 mm.

* * * * *